(12) United States Patent
Shiau et al.

(10) Patent No.: US 6,605,291 B2
(45) Date of Patent: Aug. 12, 2003

(54) THERAPEUTIC PAD AND A METHOD FOR TREATMENT OF COMMON ILLNESSES

(75) Inventors: Yen-Kuen Shiau, Taipei (TW); Chung-Hsun Wu, Tao Yuan (TW)

(73) Assignee: Parker Holding Services Corp., Taipei (TW)

( * ) Notice: Subject to any disclaimer, the term of this patent is extended or adjusted under 35 U.S.C. 154(b) by 0 days.

(21) Appl. No.: 09/918,516

(22) Filed: Aug. 1, 2001

(65) Prior Publication Data

US 2003/0035825 A1 Feb. 20, 2003

(51) Int. Cl.⁷ .......................... A02N 25/34; A62F 13/00
(52) U.S. Cl. ...................... 424/402; 424/400; 424/443; 424/447; 424/449; 424/489
(58) Field of Search ................. 424/402, 400, 424/489, 443, 449, 447

(56) References Cited

U.S. PATENT DOCUMENTS 6,051,246 A * 4/2000 Shiau et al. ................. 424/409

FOREIGN PATENT DOCUMENTS

| JP | 2000005271 A | * | 1/2000 | .......... A61H/39/04 |
| JP | 2001187108 A | * | 7/2001 | .......... A61H/39/04 |

* cited by examiner

Primary Examiner—Thurman K. Page
Assistant Examiner—Robert M. Joynes
(74) Attorney, Agent, or Firm—Chenpatents; Alice L. Chen

(57) ABSTRACT

A therapeutic pad comprises a spinel powder having the formula of $AB_2O_4$ which emits 3–18 or 3–30 micron wave length depending the composition of the spinel for treatment of pain. A novel method for treatment of pain by placing the said pad with the spinel powder over the painful area.

9 Claims, No Drawings

THERAPEUTIC PAD AND A METHOD FOR TREATMENT OF COMMON ILLNESSES

BACKGROUND OF THE INVENTION

1. Field of the Invention

This invention relates to a novel method for the treatment of common illnesses such as joint pain, headaches, insect bites, and bruises with far-infrared radiation, as well as a therapeutic pad incorporating a spinel powder, capable of emitting such radiation. More particularly, it relates to certain wave length radiation for relieving pain or related discomfort.

2. Prior Art

Inorganic spinels are known for their antimicrobial properties as shown in applicant's U.S. Pat. No. 6,051,246. Infrared radiation is known for its beneficial effects in the human body. However, no method or product using spinel compounds of the general formula AB2O4 as disclosed herein is known in the prior art.

SUMMARY OF THE INVENTION

It has now been discovered that far-infrared radiation emitted by spinels having the general formula AB2O4 have broad pain-relieving potential. No source of far-infrared radiation other than AB2O4 is known to have comparable healing properties.

The object of this invention therefore is to provide a safe product having ground spinel AB2O4 mixed with adhesive supported by a soft substrate (hereinafter referred to as therapeutic pad), and a method as taught in this invention for applying said pad to the area of the body afflicted by pain such as joint pain, back ache, headaches, insect bites, and bruises as well as arthritis, rheumatism, and other degenerative diseases of joints due to the aging process. Relieving pain in accordance with this invention is an effective remedy for reducing suffering when no other cure is available. Furthermore, this method is safe in that it is topical, non-invasive and non-reactive, causing no side effects of concern. It reduces the cost of medical treatment due to the chemical stability of the spinel, which is a source of radiation in the desired range of wavelength in the far infrared spectrum.

DETAILED DESCRIPTION OF THE INVENTION

The novel component of the therapeutic pad of this invention is a far-infrared emitting spinel having the general formula of AB2O4, wherein A is magnesium, divalent iron, nickel, manganese, cobalt, or zinc. B is aluminum, trivalent iron, trivalent manganese, or trivalent chromium. O is oxygen. The spinel AB2O4 emits radiation in the range of wavelength from 3–30 microns, which has the desired pain-relieving effect. It is further found that treatment with radiation in the 3–18 micron spectral range is preferred due to its high efficiency. In the preferred embodiment of this invention, B is aluminum, trivalent chromium, or trivalent manganese. Any of the following compounds, MgAl2O4, ZnAl2O4, CoAl2O4, MnAl2O4, NiAl2O4 or any combination of A with B as chromium, and manganese, and O4 are preferred.

The therapeutic pad is a pliable substrate coated with ground $AB_2O_4$ mixture by any method known to the art. It is to be noted that the infrared range of radiation is from about 0.75 microns to 10 microns. However, it is the far infrared range of wavelength, 3 to 30 microns, that has the most beneficial effect on human health. The preferred range of far-infrared radiation for pain relief is 3–18 microns.

It has further been found that the range of wavelengths emitted by the spinel is determined by the chemical component B which has most beneficial results in relieving pain. Aluminum, trivalent chromium, or trivalent manganese are the preferred elements in B.

The therapeutic pad comprises a coat of a paste of ground spinel mixed with an adhesive and applied in a thin layer on a pliable substrate, preferably a breathable tape made by 3M company. Any other commercially available soft plastic sheet, may also be used. The method of coating is available in the prior art. Should the substrate be a self adhesive type, then the adhesive need not be mixed with the powder spinel.

The shape of the pad can be adapted to conform with the contours of the human body. The method of treatment involves placing the pad having the coated spinel powder over the skin where the pain is and allowed to remain in place until pain is relieved.

The efficacy of the therapeutic pad having irradiation of 3–18 micro was tested experimentally and the test results are summarized in the following table. The number of patients participating in the test was 107, 43 females and 64 males. The parts of the body treated are indicated by an alphabetic code listed below the table. The time of treatment and duration of pain relief are expressed as average in hours, so are the standard variation of the measurements.

| Parts of body treated | no of person treated | time treatment, hr. (pain relief) | | pain relief duration, hr. | |
|---|---|---|---|---|---|
| | | average | standard deviation | average | standard deviation |
| a | 3 | 1.40 | 1.04 | 16.13 | 13.28 |
| b | 9 | 9.05 | 11.26 | 29.44 | 23.17 |
| c | 5 | 12.70 | 19.87 | 48.00 | 16.97 |
| d | 1 | 4.0* | | 72* | |
| e | 12 | 37.08 | 43.67 | 87.08 | 100.08 |
| f | 13 | 23.08 | 21.97 | 59.08 | 27.04 |
| g | 14 | 18.68 | 20.69 | 63.43 | 34.72 |
| h | 14 | 38.75 | 34.98 | 105.43 | 70.79 |
| i | 14 | 44.21 | 54.75 | 152.64 | 186.70 |
| j | 2 | 94.25 | 132.58 | 240.50 | 338.70 |
| k | 13 | 16.62 | 21.83 | 70.46 | 47.99 |
| l | 7 | 43.50 | 61.31 | 115.14 | 115.61 |

Notes:
*no standard deviation
Parts of body: a, temple; b, nostrils; c, tooth; d, ear; e, neck; f, arm; g, shoulder; h, back; i, lumbar, j, coccyx; k, patella; and l, ankle. Time of treatment is accumulative.

Therapeutic pads used in this experiment were made from ground spinel powder mixed with adhesive so as to give the consistency of paste. A thin coating of about ⅛ inch thickness of the mixture is applied to the surface of a breathable tape made by 3M company. The shape of the pads varied according to contour of the parts of the body.

The above table demonstrate the efficacy of the therapeutic pad and the method of predictably relieving pain from a suffering patient. The pad will remain effective for a long time due to the spinel's ability of adsorbing energy from environment and converts to different radiation energy. It does not need special maintenance or parts replacement for a period of time. The pad does not cure any underlying medical causes for aches and pains. However, any relief of pain is a great comfort to the patient. Due to its ability to promote blood circulation, the treatment eliminates any blood clots in bruises. The healing of superficial cuts is enhanced.

We claim:

1. A therapeutic pad for treatment of pain comprising a spinel powder having a formula of $AB_2O_4$ wherein A is magnesium, divalent iron, nickel, divalent manganese, divalent cobalt, or zinc;

B is aluminum, trivalent iron trivalent, manganese, or trivalent chromium; and

O is oxygen;

wherein the spinel compound emits far infrared radiation in a range of 3 to 30 micron wave length, and a pliable substrate on which said powder being incorporated.

2. The pad of claim 1 wherein the substrate is breathable tape.

3. The pad of claim 1 wherein the preferable element B of the spinel powder AB2O4 is selected from the group consisting of aluminum, trivalent chromium, and trivalent manganese, said spinel emitting radiation in the wavelength range of 3–18 microns.

4. A method of relieving pain comprising irradiating the painful area of a human body with a spinel compound which emits radiation in the 3–30 micron wavelength range, said spinel having the formula of $AB_2O_4$ wherein A is magnesium, divalent iron, nickel, divalent manganese, cobalt, or zinc;

B is aluminum, trivalent iron, trivalent manganese, or trivalent chromium;

O is oxygen.

5. A highly efficient method of relieving pain comprising irradiating the painful area of a human body with a spinel compound which emits radiation of 3–18 micron wave length and having the formula of $AB_2O_4$ wherein A is magnesium, divalent iron, nickel, manganese, cobalt, or zinc;

B is aluminum, trivalent manganese, or trivalent chromium;

O is oxygen.

6. A method of relieving pain of a human body comprising placing a therapeutic pad of claim 1, over the painful area.

7. A method of relieving pain of a human body comprising placing a therapeutic pad of claim 3, over the painful area.

8. The therapeutic pad of claim 1 wherein the spinel powder is mixed with an adhesive to form a paste which is coated on a breathable pad in a thin layer.

9. The therapeutic pad of claim 3 wherein the spinel powder is mixed with an adhesive to form a paste which is coated on a breathable pad in a thin layer.

* * * * *